United States Patent [19]

Snook

[11] Patent Number: 5,512,966
[45] Date of Patent: Apr. 30, 1996

[54] OPHTHALMIC PACHYMETER AND METHOD OF MAKING OPHTHALMIC DETERMINATIONS

[75] Inventor: Richard K. Snook, Houston, Tex.

[73] Assignee: Orbtek, Inc., Utah

[21] Appl. No.: 418,563

[22] Filed: Apr. 10, 1995

Related U.S. Application Data

[63] Continuation of Ser. No. 80,497, Jun. 24, 1993, abandoned.

[51] Int. Cl.⁶ ........................................ A61B 3/10
[52] U.S. Cl. .......................... 351/205; 351/212; 351/214
[58] Field of Search .................................. 351/205, 211, 351/212, 214, 221

[56] References Cited

U.S. PATENT DOCUMENTS

| | | | |
|---|---|---|---|
| 4,440,477 | 4/1984 | Schachar | 351/212 |
| 4,523,821 | 6/1985 | Lang et al. | 351/214 |
| 4,606,623 | 8/1986 | Schachar | 351/212 |

FOREIGN PATENT DOCUMENTS 0630607  12/1994  European Pat. Off. ............... 351/212

Primary Examiner—William L. Sikes
Assistant Examiner—Huy Mai
Attorney, Agent, or Firm—Robert J. Schaap

[57] ABSTRACT

An ophthalmic pachymeter which is highly effective in aiding in the determination of thickness and the optical density of the cornea of an eye on a real-time basis. The pachymeter therefore lends itself to effective employment in aiding in radial keratotomy and other surgical procedures with respect to the eye. The ophthalmic pachymeter of the invention has three major subsystems which include a television camera, a multiple slit projector and an associated processing and display system. In a broad form, the invention comprises illuminating a selected portion of the cornea, moving a slit across the cornea and generating Tyndall image ray paths for enabling analysis of the optical density of the cornea and the thickness of the cornea. This is accomplished through a series of digitally-encoded television images of the optical section of the cornea produced by a multiple slit projector and which images are then subjected to digital analysis. A locus of each of the significant elements of the reflected image of the anterior portion of the eye is defined. In this way, the optical character of the cornea/air interface is compared with the corrected reflectance of the stroma and the endothelium, in order to determine relative transparency. A density map may be constructed in parallel slices for display as a three-dimensional plot of the frontal surface shape of the cornea and for defining and displaying the local thickness, the posterior surface contour, and the optical density of the cornea.

48 Claims, 7 Drawing Sheets

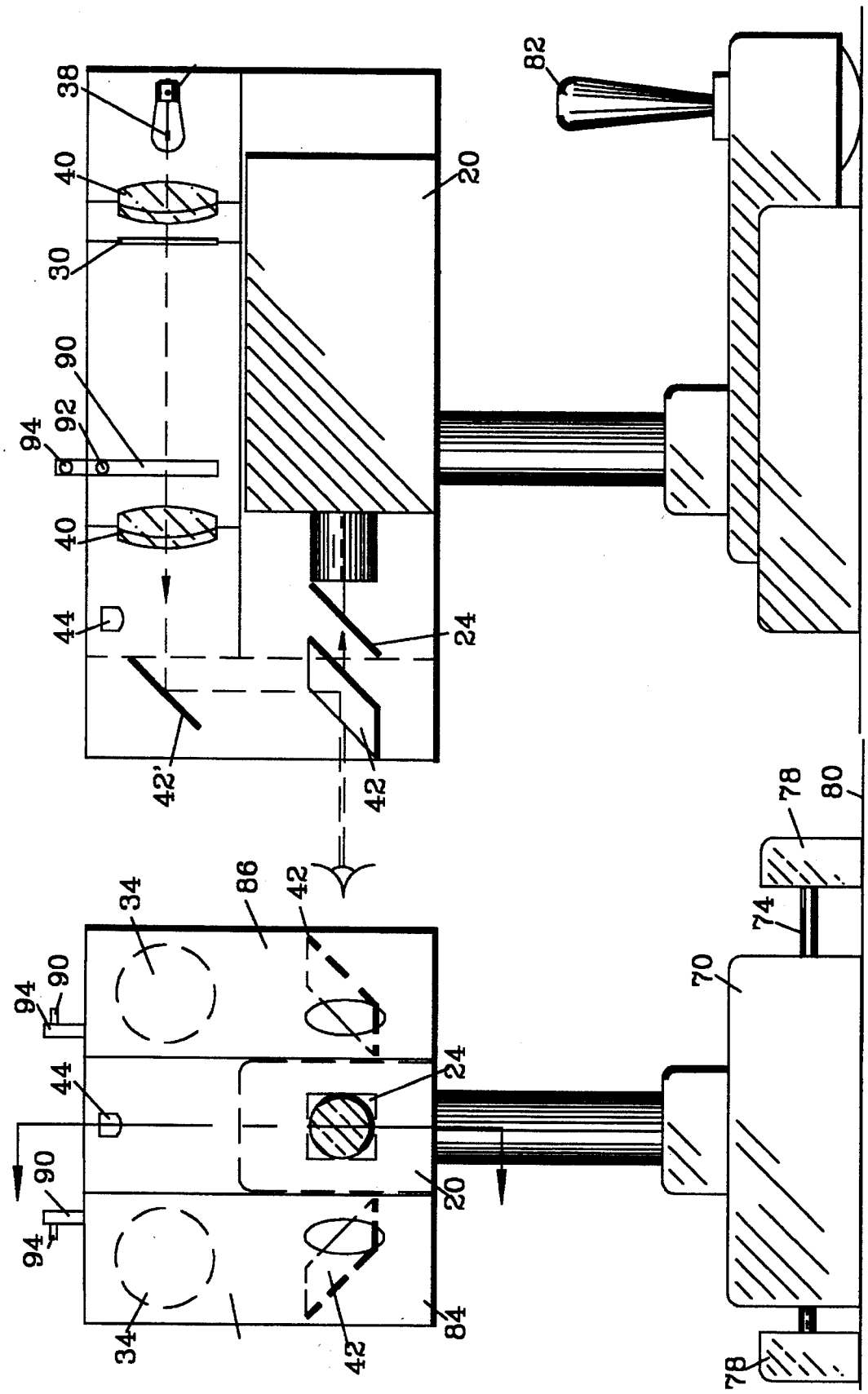

OPHTHALMIC PACHYMETER AND METHOD OF MAKING OPHTHALMIC DETERMINATIONS

RELATED APPLICATION

This application is a continuation of my U.S. patent application Ser. No. 08/080,497, filed Jun. 24, 1993 entitled Ophthalmic Pachymeter and Method of Making Ophthalmic Determinations now abandoned.

BACKGROUND OF THE INVENTION

1. Field of the Invention

This invention relates in general to certain new and useful improvements in ophthalmic pachymeters for aiding in the determination of the thickness and relative optical density of the cornea of the eye on a real-time basis and to an improved ophthalmic pachymeter of the type which primarily relies upon a television camera, a multiple slit projector and an associated processing and display systems which cooperate in a unique manner to provide a three-dimensional map of the cornea.

2. Brief Description of the Prior Art

The measurement of optical density of cataracts has been a subject which is becoming more widely addressed in recent times. One of the recent teachings of cataract optical density measurement is set forth in U.S. Pat. No. 4,863,261 to J. Flammer, "Method and Apparatus for Measuring the Extent of Clouding of the Human Eye." The prior art relating to the measurement of optical density is also exemplified in U.S. Pat. No. 4,019,813 for "Optical Apparatus for Obtaining Measurements of Portions of the Eye."

Planning for anterior segment surgery is also a topic which has received increasing attention in recent years, as, for example, in a paper by Lehrman, et al., "Measurement of Anterior Chamber Diameter" and "Biometry of Anterior Segment by Scheimpflug Slit Lamp Photography", reported in Investigative Ophthalmology and Visual Science, Volume 32, No. 3, March 1991, pages 529–532.

The slit lamp is an instrument employed by many optometrists and ophthalmologists for examination of the anterior portion of the eye. Many different versions of the instrument have been produced over the last century, but all of the slit lamps have three major elements in common and which include a projector for providing a collimated image of an optical slit focused on the eye, a bio-microscope or camera for viewing the image and a mechanical support system. In this slit lamp system, the bio-microscope or camera is designed to view the image formed by the projector and is confocal with the projector. The mechanical support system must be elaborate to at least support the subject and the projector and viewing system. Furthermore, the elements must be positioned relative to one another for appropriate examination of the eye.

Pachymetry attachments are available for the slit lamp to be used in clinical environments. These attachments operate so as to displace half the image by a plane parallel glass block interposed in the viewing path. In this way, corneal thickness is measured at a single point. The reading of the drum forming part of this attachment is then recorded by hand as the local corneal thickness. While these modified forms of slit lamps, which operate as pachymeters, can accurately define corneal thickness at an unknown location, they are slow, expensive and fragile. Moreover, they are quite difficult to operate, and require substantial training on the part of the operator.

One of the most common corneal thickness measurements used in clinical practice today is that of ultrasound. The A-scan ultra sound probe, much the same as with the optical pachymeter, produces a single-point measurement at an unknown locus of the cornea. In addition, this unknown single point is, in reality, the average thickness of an area of several square millimeters in extent. Because the location of the measurement is not repeatable, the data is variable as well.

One of the principal problems of the prior art systems is that the plots which one generated to provide a cornea mapping were not accurate and more importantly, were not repeatable. Thus, the prior art did not provide the ophthalmic surgeon with the data required for planning radial keratotomy or other refractive surgical processes.

Some of the other deficiencies in the prior art techniques used for determining corneal thickness and mapping is hereinafter described in the following Overview Of The Invention. In this Overview Of The Invention, the prior art is, in some cases, also contrasted with the principles of the present invention in order to more fully show the substantial advantages achieved by the present invention. Also, and to some extent, background theory is set forth in order to more fully aid in the understanding of the present invention.

OVERVIEW OF THE INVENTION

Densitometry is a term applied to measurement of the optical density of areas of photographs. Densitometers commonly measure the log of the reciprocal of the percentage of light transmission for a defined area at a stated wavelength or wave band. Measurement of the relative reflection of scattered light is commonly employed to define turbidity in water samples. The amount of light scattered and thus retro-reflected is thereupon compared to a known reference value in this process, in order to determine scattered light reflection.

The densitometer of the present invention measures the relative amount of reflected light from scattering within ocular tissue as an indication of the optical density. In the strictest sense, this is not a true density measurement but is a measure of the relative transparency of the corneal tissues. The corneal interface with the air is not affected by stromal opacification and serves as a relative density reference for the measurement. The minimum reflectance value for calibration is derived from the signal representing the anterior chamber over the pupil where the average reflectance is the smallest. Optical density of small and large areas of the cornea often provides diagnostic data for deciding the need for surgical intervention. In addition, surface contour and the thickness of the cornea are quantified for producing a complete, three dimensional thickness map of the cornea including local thickness of the membrane.

The present invention utilizes light from an incandescent lamp for analysis of the thickness and optical density of the cornea at one or more wavelengths. By making successive exposures with a small linear movement of a slit image between each exposure, a series of slice density images can be generated. These images are then stored in a digital format. The displayed reconstruction of these slices is similar to that used in computer axial tomography and light processes which are now well known in the art. From this three dimensional display, the anterior chamber depth and local corneal thickness may also be seen, and this can be used in planning anterior segment surgery in accordance with the proposal of Lehrman, et al., supra.

The present invention is also effective for mapping localized opacities and used in planning corneal replacement surgery. Corneal wounds and ulcers can also be mapped to provide accurate diagnostic information to the physician by use of the pachymeter of the invention. Changes in index of refraction associated with scaring or ulceration create foci of light scattering and loss of transparency. The index of refraction in the bulk of the cornea is less in the fluid than in the fiber cytoplasm and scattering results from the optical discontinuities. The cornea may be damaged by disease processes, mechanical forces or foreign object penetration. In these cases the opacification is probably due to the changes in protein molecule orientation at the injury site in healing. The degree of opacification can be monitored by loss of visual acuity but the loss of night vision due to loss of image contrast may be debilitating occasionally where the Snellen acuity is only slightly affected.

The ability of the present invention to quantify the degree of opacification and measure the locus of any localized changes provides a tool for assessment of corneal disease and scarring. Sometimes, the localized changes in refractive index may be located away from the optical center of the cornea and may not interfere with vision to any great extent. In these cases there is a high probability of degeneration of visual acuity over time, although the traditional Snellen test does not indicate any current loss of visual acuity. Localized opacifications may also produce monocular diplopia due, in part, to diffraction at the edges of the opacification that may be masked by the constricted pupil in conventional testing methods. Testing of contrast acuity and testing of low light level, when such opacities exist, tends to show the loss of night vision adequate for safe driving and precedes the loss of Snellen acuity.

Slit lamp examination will reveal the presence of these abnormalities but direct visual examination does not provide accurate and repeatable assessment of the lesion location, density, area and any changes in size or opacity with time. The present invention provides a tool for repeatable assessment of potential vision loss under adverse lighting conditions.

A beam of sunlight entering a darkened room through a hole in a curtain or shining through a hole in a cloud forms a visible path due to dust particles, water droplets and smoke in the air. The same principle is used in slit lamp examination of the eye where the scattering of light in nearly transparent tissues renders visible structures that cannot otherwise be seen. Focal illumination is employed in the present invention by a modified conventional Köhler projector. The object at the focal plane is one or more optical slits that may be moved either manually or by an associated computer controlled mechanism. The image of each slit is made confocal with a television camera that forms a part of the pachymeter of the present invention so that the instrument may examine various areas without repositioning the instrument. The focal length of the projection lens is as long as possible to reduce the convergence or divergence of the beam over small axial distances. Projection lens focal ratio is calculated by well-known techniques for producing optimal brightness and sharpness of the illuminated area. The projector and the camera are mounted on a common vertical member to allow the projected thin sheets of light to enter the eye at an angle to the camera axis and to permit horizontal, vertical and axial alignment with the eye. The beams of light produce diffuse reflection from each successive portion of the anterior part of the eye through which it passes. Proper selection of slit width and position produces the illusion of a cross section of the cornea as a luminous band against a dark pupil.

The "Tyndall phenomenon" is the term employed to describe this method for generation of an optical section of the eye that is well known in the ophthalmic art. The diffuse reflection from the first of the layers of the cornea that provides the optical section image is used in the present invention as a reference against which the diffuse reflection from the other portions of the cornea are compared for determining the relative transparency.

The camera system commonly used to make slit lamp photographs is a single lens reflex, 35 mm camera back. The camera back receives an image through a beam splitter attached to a slit lamp microscope. For some types of anterior photography this system works well and is simple to operate. A motor film drive in the camera back and direct viewing capacity, in particular, are of great value in this type of instrument. It can be seen that there are inherent limitations in the prior art camera system which are addressed in and solved by the system of the present invention. The lack of depth of field prevents adequate effective resolution for meaningful measurement of the image. In addition, the optical system of the bio-microscope degrades the image in both resolution and light gathering power.

The present invention does not use the conventional bio-microscope of the common slit lamp, but rather employs a television camera system for producing digital images for analysis of the anterior portion of the eye. The correlation of a sequence of fixed image individual photographs is difficult. This is due to the change of fixation of gaze relative to the optical axis of the camera caused by the long time required to reposition the camera system for each image acquired. The resulting non-orthogonal picture series is difficult to interpret. The present invention solves this problem by employing a rectilinear scan system to provide rapid density and thickness measurement of the entire cornea in an easily comprehended format.

The width of the slit may be increased to provide greater illumination to compensate for the exposure loss due to small lens apertures. The slit width is preferably near 0.8 millimeters. When photographs of objects close to the camera are made, the depth of focus is dependent upon the lens focal length and the iris opening. In ophthalmic photography with a conventional slit lamp camera there is little choice over iris opening and none over focal length. The design of the instrument imposes severe light losses and provides at best about an f-16 lens opening. The use of a single lens system in the present invention permits focal ratios of f-2.8 which, in turn, permits a considerable reduction in illumination levels and consequent reduction in the possibility of photo-toxicity. In the preferred embodiment, the magnification ratio for the slit projectors is 1:1 and the camera magnification is 0.25:1. These provide the desired image for analysis with good overall focus.

The ophthalmic pachymeter of the present invention measures the elemental brightness of a selected portion of a Tyndall image of the eye. Selection of a portion of the field of view of a slit lamp system is accomplished with computer control through the use of a table of valued fiducial marks delineating selected areas in the video display. The instant slit location and angle are computer controlled and the highest Tyndall arc is definable in terms of known maximum curvature of the human corneal surface. These data permit the selection of a band of picture containing the Tyndall image to be digitized, stored and used for construction of the corneal surface models for display. The elemental amplitude within the delineated area is determined by subdividing the video image line segments selected into small picture elements or "pixels" which are examined and quantified for brightness information.

In the system disclosed in the present invention, a "clock" signal is derived from a highly accurate crystal controlled oscillator to provide subdivision of the raster lines into well-defined time/size elements. The preferred embodiment uses a medium resolution solid state television camera. The lower inherent resolution, as compared to a 35 mm film, is adequate for mapping the eye for most clinical applications and provides better long term stability than tube type television cameras, while requiring minimal storage and processing time.

The present invention provides a system for further reducing the number of loci used in the calculations involved in the mapping by circumscribing portions of the visible frame to encompass the area of interest. In this way, the resultant information is stored in more compact form without loss of resolution or accuracy. The gamma curve for film images shows the relationship between log exposure and log density of the image. In a video based system the gamma curve may be tailored by methods that are well known in the television signal processing art, for optimal data derivation. In the video amplifier used for the television camera interface the gamma curve, can be made to vary with amplitude that is a function of log exposure. The high inherent sensitivity of modern television cameras, together with the ability to shape the gamma curve for calibration in the present invention, thereby provides a considerable improvement in raw data quality over the photographic process of the prior art.

Because the brightness of the tyndall image of the cornea differs from the almost constant anterior corneal surface reflex, a simple numerical amplitude discrimination process is used to define points within the circumscribed fiducial area. These brightness values together with the X, Y locus of these pixels is the only data stored for the pachymetric measurements. The numerical values for the pixels so defined are then used to define the optical density in terms of relative scattering of light by location within the cornea. The optical density is further corrected by compensating the measured brightness of each pixel for the losses due to the density of portions of the path through which the illuminating and scattered light traverses and by conventional gamma correction circuitry. Histogram correction or other well-known techniques may also be employed for enhancing the values defined for the Tyndall image which is stored in digital format.

The shape of both anterior and posterior surfaces and the thickness of the cornea of the human eye can be mapped by means of the slit projection system of this invention. The line of gaze fixation is made coincident with the optical axis of the camera by a target viewed by the subject via a beam splitter. The beam splitter and fixation target are so positioned as to cause the desired alignment of the eye and camera, and thus, the slit beam. The coaxial location of the fixation target insures that the visual axis of the eye being examined is coincident with the optical axis of the television camera. Beams of light formed by projection of an optical slit or slits are focused at or slightly behind the corneal surface. The beams are projected from known points located on a line at a fixed angle, preferably 45 degrees, from the optical axis of a camera and in the same plane.

At normal incidence, the reflection of light at a boundary between media of differing index of refraction is calculated as follows:

$$R=(n_2-n_1)^2/(n_2+n_1)^2$$

Where R is the reflected percentage of the incident beam, and, $n_1$ and $n_2$ are the indexes of refraction of the two media respectively. From this it follows that the air to cornea and cornea to aqueous interfaces will reflect a definable portion of the slit beam diffusely. The stroma or interior structure of the cornea comprises large muco-saccharide molecules in lamellar arrangement with surrounding saline solution. This causes a similar diffuse reflection of part of the incident beam and produces the so called "Tyndall" phenomenon. The tyndall image is therefore the result of diffuse reflection at the optical discontinuities in the slit beam path. Because the locus of origin of the slit beam relative to the optical axis of the camera is known, the shape of the Tyndall image as viewed describes the shape of the cornea. Taking a point on the Tyndall image, there is a displacement from where the slit beam would have intersected the reference plane that corresponds to a function of the height of the surface at the datum point.

After generating the anterior surface of the cornea the posterior surface can be defined using the refractive index of the cornea and the angle of incidence for each ray derived from the anterior surface data by application of Snell's law. The beam is refracted into the denser medium by an amount calculated from the relative slope at each calculated ray entrance. The light from the slit projector is also reflected by the corneal/air interface in a specular manner. This reflex provides a check of the contour generated from the Tyndall data. The local slope of the cornea can be taken to be equivalent to a sphere of some radius when the surface area is very small. The resulting spherical mirror formed will act to reflect the incoming ray from the projector(s). The location of beam source and relative angle provides the basis for calculation. The image of the reflection is located in X, Y coordinates from the digitized image and the slope at the surface is calculated by the methods used by Placido that are well known in the art. This independent method slope derivation at points on both sides of the cornea, generally midway between the center and the limbus, provides quality assurance for the Tyndall image derived surface shape.

Calculation of the surface shape in the present invention is performed by means of analysis of similar triangles, as illustrated in FIGS. 13 and 15. The anterior surface contour is defined first. The method involves simple geometric analysis of the Tyndall image. The angle between the slit beam and the optical axis is fixed at 45 degrees at center. The distance between the mirror and the eye is also fixed at a known distance. The image point for each pixel is displaced from the optical axis as a direct function of point height above the reference base plane. In the preferred embodiment of the present invention the image to be analyzed is produced by projection of narrow bands of light into the eye by optical projectors of conventional "Köhler" design.

In the conventional slit lamp, the bio-microscope and slit projector are mounted on pivoted arms with a common bearing center so that the microscope and projector may be independently rotated in the horizontal plane while remaining confocal. In the present invention this arrangement of elements may be replaced by two slit beams from opposing sides with a constant angular relationship to the eye and camera. The image of Tyndall illuminated areas of the slit or slits are formed in the plane of focus of the camera. The slit beams are angled-to produce edge convergence of the Tyndall images when the axial distance between the central point of the cornea is at the desired distance and the camera focal range lies from this plane at or near the iris to a more anterior plane beyond the corneal anterior surface. This construction provides the requisite known distance for all calculations and provides a simple operator clue to proper centering and focus.

The projectors of the present invention are fitted with internal filters for establishing the spectral content of the beam of light projected into the eye. The use of selectable filters to limit the spectral distribution of the illuminating beam provides the ability to quantify discoloration of portions of the cornea associated with age, scars or disease processes while limiting any potential photo-toxicity from the light energy within the globe. In an alternative embodiment, the filters are designed to pass only the near infra-red portion of the spectrum which makes the slit beams invisible to the subject.

The projector used with the present invention is additionally provided with a mechanism for providing slit motion. In the preferred embodiment, the slit assembly is moved under computer control in a direction perpendicular to the long axis of the slit when sequential image data slices are required. The slits are initially centered and projected from both sides simultaneously. The resultant dual Tyndall image is used for determining instrument position to assure accurate focus and known magnification. The operator positions the instrument so that the center of the two arcuate images is coincident and centered in the pupil. The construction of the instrument then provides the proper focus for the image series that comprises the pachymetric measurement.

In one of the preferred embodiments, as previously mentioned, a pair of projectors are employed and each move an individual slit assembly. Further, each slit assembly is moved under computer control perpendicular to the longitudinal axis of the slit. Each slit is also moved from an opposite side of the eye.

In another alternative embodiment the optical slits are formed by ferro-fluidic type liquid crystal devices. The liquid crystal system is faster and dissipates less power but provides less flexibility of slit locus for special diagnostic use.

The signal from the television camera is used to derive the relative image brightness of the corneal optical sections while the optical figure is being digitized and also viewed on the television monitor. Monitors for viewing both pictorial and computer signals are well known in the art and are not described herein.

Repositioning the slit beam by incremental motion perpendicular to the slit axis permits measurement of almost all of the cornea in detail and the composite time domain image data sequence is stored for analysis and display. The slit motion is interlocked in time with the vertical interval of the camera so that the successive images are stored over a very short interval and so that loss of fixation or micro saccadic motion of the eye does not degrade the data.

The television sync signals cause an internal oscillator in the display system to be synchronous with the computer and camera and consequently, the data sequence. Each video line requires a fixed, known time. The action of a video analog to digital converter, called a "frame grabber", serves to quantify the instantaneous brightness related voltage amplitude of each image element and to store the sequence in a memory for later use.

Subdivision of the video line into small spatial elements or pixels is by time interval selection. The intervals are defined by a stable clock oscillator that provides a series of pulses which correspond to image loci. The line rate and the clock rate define the size of a pixel in terms of pixels per line or pixels per second. In conventional broadcast television, the signal is limited to 4.5 Megahertz, which yields a pixel rate of only 236 for the active or visible line of some 52.4 microseconds, although the overscan of the display means that even fewer pixels make up the actual image viewed by the user. A computer generated display is structured in similar fashion to make use of components that are in volume production.

The present invention makes use of a common commercial camera and monitor apparatus without modification. Because the cornea of the eye is essentially circular in form, the normal television picture aspect ratio of a 4:3 ratio or a 5:4 ratio, employed by many computer displays, provides no advantage. In operation, the use of computer displays for television pictures deletes some of the picture in the horizontal axis. This "cropping" is of no consequence in the present invention. The most common camera tube is two-thirds inches (approx. 18 millimeters) in diameter. The desired image is roughly eleven millimeters in diagonal or somewhat less. This assumes the diameter is equal to the height of the image. The image sizes for the other common tubes are, 16 mm for the one inch tube and 8 mm for the one-half inch type. The focal length of the lens and the size and location of the fiducial mark generation is determined on the basis of a square area that nearly fills the frame with the image in the vertical direction. The analog to digital conversion is usually, although not necessarily, limited to a square area with a width equal to the largest commonly found limbus that is about 12 millimeters. The inner edge of the iris opening is also visible in the captured images and because the light does not always enter the pupil, the iris changes size during the measurement. The shape and rate of iris motion are often of clinical interest and can be generated through an additional computer program in an alternative embodiment that is not illustrated or described.

For highest accuracy, each instrument must be calibrated after assembly to compensate for minor differences in system magnification and linearity to obtain maximum accuracy of the derived data. For this reason calibration objects and programs are provided as a part of the computer software so the user may check the calibration and reset the table values at any time.

The actual measurement of the image is by the process of subdividing the television image raster line into small elements of time that are examined for brightness information. A relative magnitude decision is based on these bits of data and represents relative brightness for each information pixel within the selected area. A signal is generated by the computer display driver to control the display system used for operator interface. The signal complex comprises horizontal and vertical synchronizing signals, blanking signals and the pixel brightness data for the information to be displayed, as described above. The synchronizing signals are used in the present invention along with the basic timing signal called "dot clock". The dot clock is derived in the computer or frame grabber from a crystal controlled oscillator and, together with the synchronizing pulses, defines the locus of each pixel in the image. These signals are used to assure the synchronism in time and therefore spatially of the data to be analyzed in the present invention.

One of the display functions commonly available from computers is the so-called graphic format in which lines may be positioned on the display screen under software control. The present invention makes use of this ability to define part of the image from a camera synchronized to the computer display that contains the image of the cornea to be defined. The computer controlled slit movement signal is coordinated with the data masking function to define the portion of the image for computer analysis. Only those pixel loci that define brightness within the defined margin are stored. This technique reduces the number of data points to compute, increases speed and reduces artefact signal induced error in the analysis.

The present invention may also use shading corrector circuits of conventional design to eliminate artefact signals that can be generated by the "black" level offset and the nonlinearities introduced into the video signal by some types of camera protective circuits. The shading signals are the first and second derivatives of the synchronizing pulses with adjustable polarity and phase that are algebraically added to the raw video signal before quantizing.

A table is constructed to provide a lookup technique of conversion for a range of measured brightness representing a range of known optical density. This table may be constructed with values to obtain any required degree of precision and thereby assure accurate output data for the intended application. The lookup table is constructed in a histogram analysis step where anterior surface reflectance is measured and the relative values which are obtained are then stored. Extrapolation between table entries is quite practical and reduces the number of table entries needed to assure accurate measurements.

The micro computer has provisions for graphic displays of bit mapped information in terms of X, Y coordinates on one of several pages of display memory. These data may take the form of pictorial and/or text type images in storage. Whole pages or portions of pages may be called for display on a frame by frame basis. The magnification to be used for the camera of the present invention is fixed and consequently the area encompassed by the optical section and the constituent pixels are definable in terms of X, Y coordinates for all elements of the areas defined. The initial data sample is masked by selection of only that section of the image data that defines the corneal image. Each of the subsequent data samples that represent corneal sections are defined by a second range of loci that encompasses only the area of the Tyndall image. The pixel clock from the computer display system defines each pixel in storage and in the display.

Computer generated alignment points, or so-called "fiducial points", are displayed with the picture of the eye. These fiducial points are placed over the corneal image by movement of the instrument by the user. The operator moves the instrument until the corneal image lies within the defined area, focuses the camera by axial motion until the desired focus figure is centered on the limbus within the frame, and then operates a switch to accept the data sample and to initiate the data collection sequence.

The light reflected from an optical discontinuity, such as the corneal surface, can be calculated by use of the formula set forth above for determining a reflected percentage of light. In this case, the values of index of refraction, n, are 1.000 for air, 1.333 for the tear film and approximately 1.376 for the cornea and 1.34 for the anterior chamber fluid. Thus, it can be seen that only a small fraction of the incident light will be reflected by the normal cornea. The losses are calculated in the computer program to normalize the corneal image data for determination of the effective optical density of image points in the optical section.

In an alternative embodiment, a color filter is inserted in the projection path for reducing the blue end of the spectrum to enhance the contrast ratio due to blue or grey iris coloration if present. In another alternative embodiment, the filters pass only near infra-red light so that the subject is unaware of the measurement and so that the iris reflex is not stimulated.

The radius of curvature of the cornea is measured in the typical clinical practice by an ophthalmometer or keratometer. The image of an object of known size is observed as a reflection from the corneal surface. This convex mirror provides the data required for the calculations. In practice, the value of the sagittal height V, is small relative to the axial distance u and is ignored. The use of cylindrical targets in some devices complicates the calculations and, in general, produces rather poor results due to the number of assumptions and approximations in the derivations.

By referring to FIGS. 13 and 14 of the present invention, as hereinafter described, it can be seen that the object AB is an erect virtual image ab in the plane defined by sagittal height V. The magnification is negative since the mirror formed by the corneal surface is convex. Then, $ab/AB=I/O=V/u$ and since $i/f= 1/(r/2)$ then $1/V+1/u=2/r$. Eliminating V by solving for $1/V$ and substituting produces: $O/Iu+1/u= 2/r$, from which the radius of surface curvature at the point of image measurement is calculated as $r=2 \cdot u \cdot I/O+I$. Because the ratio of object size to image size is large the simplified calculation $r+2uI/O$ is used in most calculations.

There are several fallacies in the calculation even before the curvature is transformed into dioptric terms for use by the physician. The inherent assumption is that the surface is spherical and that in constructing a corneal surface map the central point is accurately defined. In fact neither of these conditions obtain in the clinical setting. The central point cannot be derived because the instrument has a camera lens centered in the object that is a series of concentric circles illuminated from behind. The presence of the lens prevents measurements near the center of the cornea but the map is constructed as a set of equivalent radius points from which slopes are defined relative to the central point that is not measured. This requires that the central surface be assumed to be perfectly spherical which is rarely, if ever, the case.

In addition to the fact that the surface is not usually spherical, the lensmakers formula used as the basis for the computation is only true for paraxial rays and the error increases as the marginal rays are considered for surfaces removed from the center of the corneal mirror. The results are commonly expressed in dioptric form that introduces an additional error in that the corneal thickness and rear surface are unknown. The conversion of approximated surface shapes to focusing power in dioptric form uses a constant to adjust the value for better representation of the true focusing power. However, the fact that several manufacturers of keratometers and ophthalmometers use differing constants and, in some cases, tables of correction that are quite non-linear, demonstrates the inefficacy of the method. To express the focusing power of the cornea in dioptric terms the area so described must be a spherical surface and the corneal thickness and posterior curvature must be known. Even when the true corneal geometry is known, the non spherical surface over the area of the entrance pupil of the eye means that any dioptric representation is probably only an approximation and cannot serve as a predictor of focusing power.

In calculating the posterior surface, the displacement of the projected ray by the refraction of the cornea must be included. Referring now to FIG. 14, the virtual image of the slit at the posterior corneal surface is laterally displaced by an amount that is related to the angle of incidence and the local tissue thickness. The rear surface distance D' is derived from the incident ray angle $\Phi_i$.

The entering ray from A (see FIGS. 13-15) exits as a reflection at G along path 1. The ray also enters the medium n and is deflected to point H by refraction. The ray from H, in turn, exits at I along path 2. Looking back, the object appears to be located at both C and F. The distance desired, t, is derived from the following:

from triangles ABG and BGC, ∢AGB=∢BGC because they are both complements of $\Phi_i$. Therefor, BC=D.
Then BG=D tan $\Phi_i$, BI=BF tan $\Phi_i$ and GI=2t tan $\Phi_r$.
BIF and BGC are also equal to $\Phi_i$ and so, it follows that; (BG+GI)/BF=BG/D since BI=BG+GI and BC=D. Rearranging, (BG/BF)–(BG/D)=–(GI/BF) and substituting for GI, (BG/BF)–(BG/D)=(–2t tan $\Phi_r$)/BF=(–2t sin$\Phi_r$)/(BF cos$\Phi_r$).
Using Snell's law, (sin$\Phi_i$/sin$\Phi_r$=n); (BG/BF)–(BG/D)–(2t sin$\Phi_i$)/(n BF cos$\Phi_r$) and, BG=D tan$\Phi_i$=(D sin$\Phi_i$/cos$\Phi_i$). Which leads to;

(1+(2t/ND))•(cos$\Phi_i$/cos$\Phi_i$)(1/BF)=1/D and

BF=D(1+(2t/nD)(cos$\Phi_i$/cos$\Phi_r$)

The distance required is,JF which is derived, in turn, by, BF–BJ=BF–t. Then, substituting, t=D(1+(2t/nD)) (cos$\Phi_i$/cos$\Phi_j$)–JF Classic mathematical image analysis requires that groups of "pixels" or picture elements be examined as a matrix to find the location of each portion of the reflection in two dimensions and a numerical value of relative image brightness for each. With suitable computer programs, this technique provides the data for the generation of a three dimensional model of the cornea or lesion to be measured.

Thickness determination is based on a ray-tracing principle. Since the entrance angle of the ray from the keratometer is known, the index of refraction defines the ray path in the cornea. An intersection of this ray path with a ray backtraced from the camera provides an angle of incidence from which thickness determination is a trivial solution.

The surface contour of the cornea is also generated by the pachymeter of the present invention. The use of ultra-sound measurements in conjunction with the data derived from the present invention provides information to the cataract surgeon for intraocular lens selection. The main light focusing power of the eye is provided by the cornea and the fluid filled anterior chamber in front of the crystalline lens. The posterior surface of the cornea forms a lens which adds to the focusing power of the corneal anterior surface to air lens. For this reason the anterior corneal curvature provided by conventional keratometers cannot provide an accurate measure of corneal focusing power even though the measurements are expressed in dioptric terms. The present invention provides both surface shapes so that an accurate measure of focusing power in diopters is made available to the user for surgical planning.

The present invention provides a repeatable record of the corneal contour and thickness for inclusion in the patient records and improvements in accuracy and speed that are requisite for clinical use.

BRIEF SUMMARY OF THE DISCLOSURE

Generally speaking, the present invention generally provides both a new system for measuring corneal thickness and optical density, as well as a process for measuring the corneal thickness and optical density. The system and the method both provide relative transparency mapping of may types of lesions of the cornea. The invention further provides pachymetry with an almost instant display of the data to permit assessment of need for surgery. Thus, one of the important contributions of the present invention is that it essentially operates on a real-time basis, rendering almost immediate results.

The pachymeter of the present invention, as indicated previously, constitutes three major subsystems which are a modified slit lamp for projecting beams of light onto the eye to be examined, a television camera and lens system for obtaining the image of the eye and electronic circuitry for defining and quantifying a portion of the television image. Drive mechanisms are also provided for moving the optical slit to produce successive images for analysis. Associated computer software performs the requisite drive mechanism control, image selection, digital conversion of the analog television signals for computer processing and numerical analysis. This converts the information into a viewable measurement of surface shape, thickness, optical density area and even a display of derived information for clinical use. Obviously, a video output could be connected for display teaching and/or record keeping.

The clinical pachymeter of the invention also includes amplitude detection circuitry to derive the locus of image brightness discontinuities which may be associated with a lesion. The invention includes memory storage for these image points which are digital representations of a magnitude of the image brightness discontinuities. These image brightness discontinuities exist in pixel terms. A conventional electronic computer is used to derive the relative optical density and thickness profile of the cornea. The pachymeter of the present invention also generates a display of the derived density and thickness information for immediate use.

In broad terms the invention can De described as an ophthalmic pachymeter for aiding in the determination of the thickness, surface contour and transparency of the anterior segment of an eye. The ophthalmic pachymeter comprises, in broad terms, a light projecting means, such as a projector, for illuminating a defined area of the cornea. An imaging means, such as a television camera, provides for a television image of selected portions of the illuminated area of the eye. A video means, such as a video amplifier, receives the image of the eye and generates and transmits a video signal representing the image of the eye.

The video signals, which are derived by the video means, operates in conjunction with a converter means for converting these video signals into a digital format. The converter means may adopt the form of an analog-to-digital converter which operates in conjunction with a computer having a data memory. A fiducial means delineates portions of the video image for focusing and alignment. A suitable computer program delineates these portions of the video signal to be converted into this digital format. Finally, an analysis means is provided for detecting and storing the relative brightness levels within the delineated areas in the aforesaid data memory. An address counter is also employed to enable subsequent addressing of the stored information.

The present invention also relates to several processes associated with the finding of thickness and relative optical density of the cornea of the eye, as well as ascertaining extent of lesions or other optical discontinuity. In one aspect, the invention comprises a method for ascertaining the extent of the lesion or other optical discontinuity of the tissue of the eye. This method utilizes the steps of illuminating the tissue area to be analyzed. An image is generated and this image is quantified. Portions of the image which contain the lesion are delineated and a reference area is also delineated. Thereafter, the delineated areas of the image are converted into digital form for subsequently analyzing the numerical magnitude of the digital form data.

In another aspect, the present invention provides for a method of ascertaining the surface shape and local thickness of the cornea of the eye. In this case, the method involves selectively illuminating the tissue area of the eye and quantifying the image of that tissue. Again, portions of the corneal image are delineated and a reference area is also delineated. These delineated areas are then converted into digital form for subsequent analyzing of the relative numerical magnitude of the digital form data.

The invention may further be described as a system for producing surface contour maps of the cornea of the eye and comprises projection illumination means for producing a definable spacial delineation of corneal contour. A television camera means renders the illuminated areas into electrical analog form signals. The analog signals are converted in a digitizing means for computer-legible operation. A computer means calculates the corneal surface shape from the digital signals.

The preferred embodiment of the pachymeter of the present invention makes use of "bus-cards" in a PC type microcomputer to provide fast and accurate measurements and requisite motion control without the apparatus associated limitations of the prior art systems. In an alternative construction, the processor and display can be constructed as a dedicated instrument at lower total cost to fabricate but with lesser capacity to do other tasks. With careful use the system will consistently provide information to the physician to quantify corneal thickness and optical density and to map the surface shape of the eye. Several computer generated data display formats are made available from a numerical area or average density and thickness to computer monitor displays such as a wire frame pseudo three-dimensional representation, color coded thickness map or other depiction of the area of interest allows the physician to select an appropriate type of information presentation.

This invention possesses many other advantages and has other objects and advantages which will become more clearly apparent from a consideration of the forms in which it may be embodied. The following detailed description and the accompanying drawings illustrate one of the practical embodiments of the invention, although it is to be understood that this detailed description and the accompanying drawings are set forth only for purposes of illustrating the general principles of the invention. Thus, it is to be understood that the detailed description and the drawings are not to be taken in a limiting sense.

BRIEF DESCRIPTION OF THE DRAWINGS

Figure 1:
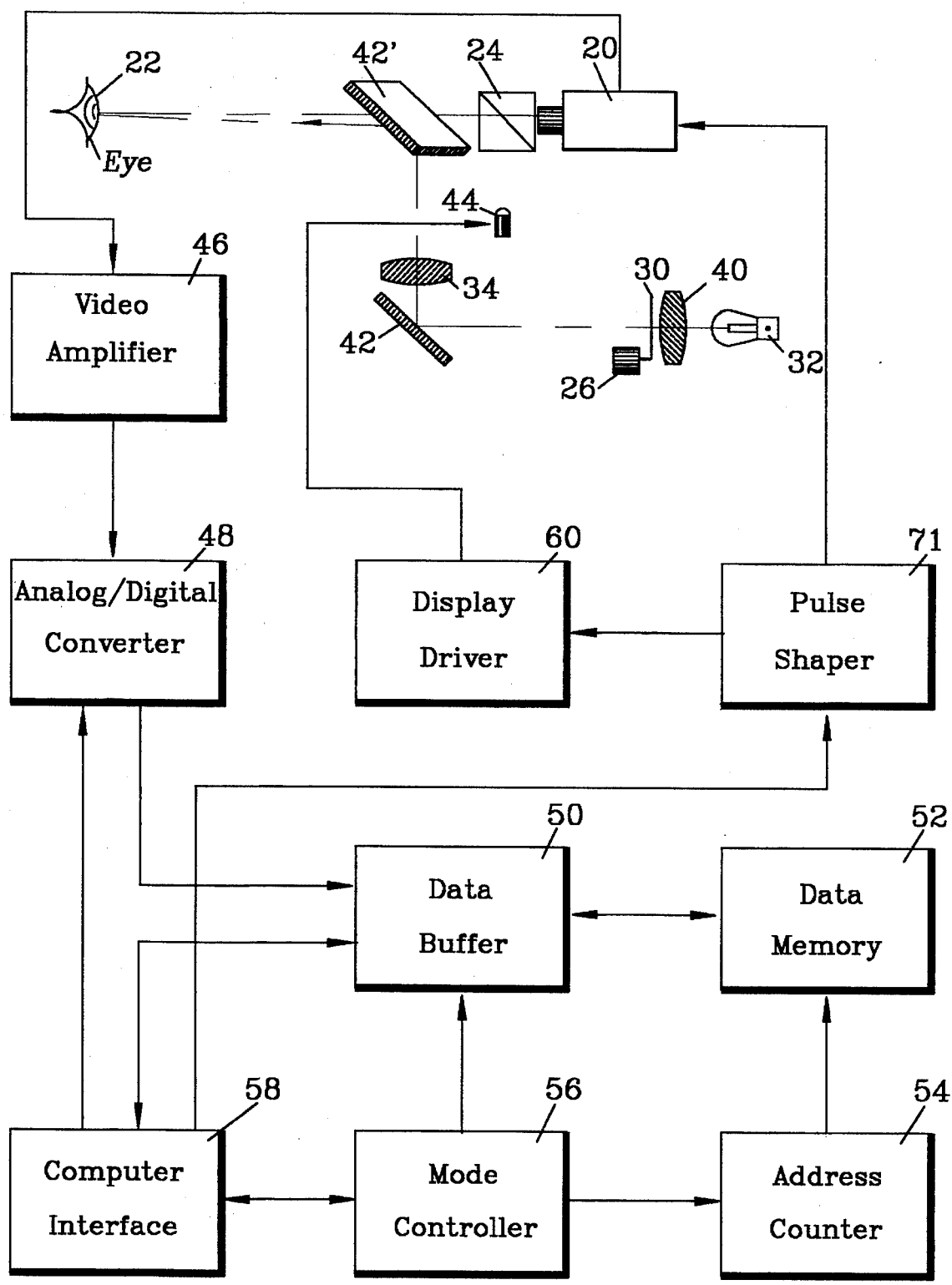
Figure 3:
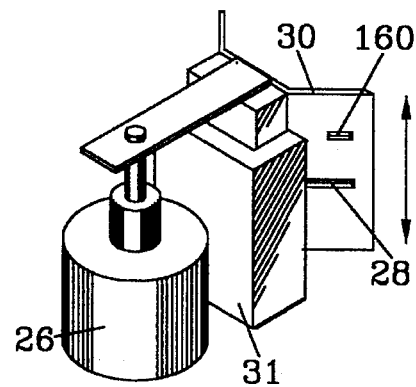
Figure 2:
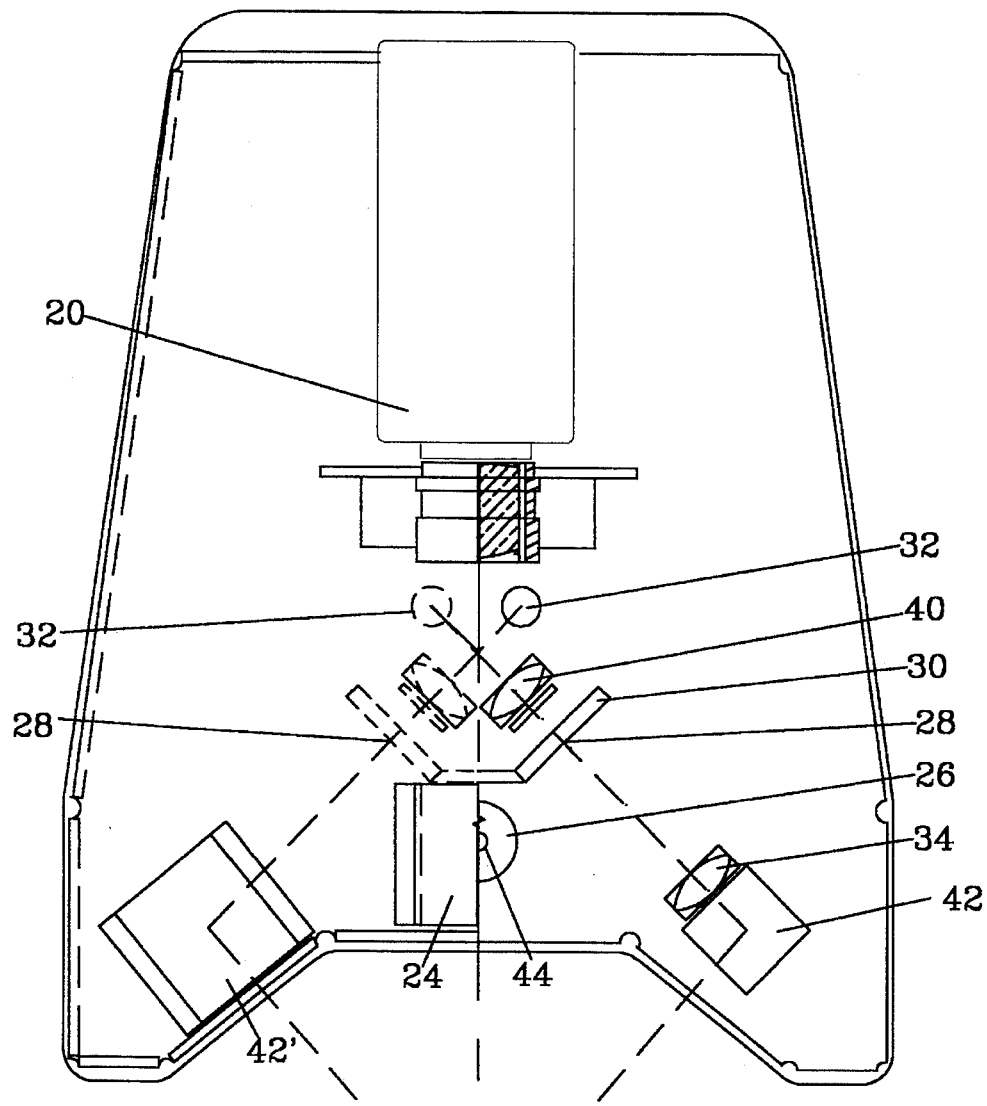
Figure 11:
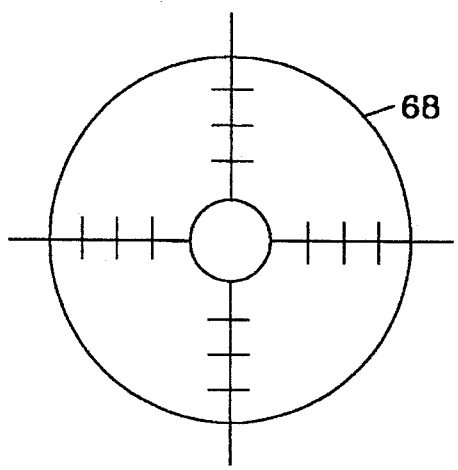
Figure 13:
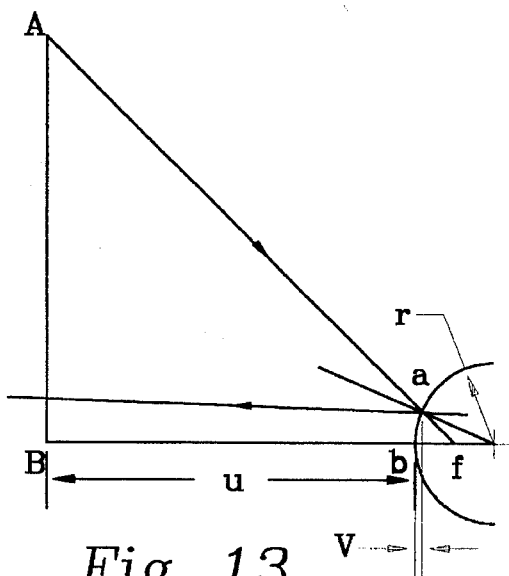
Figure 12:
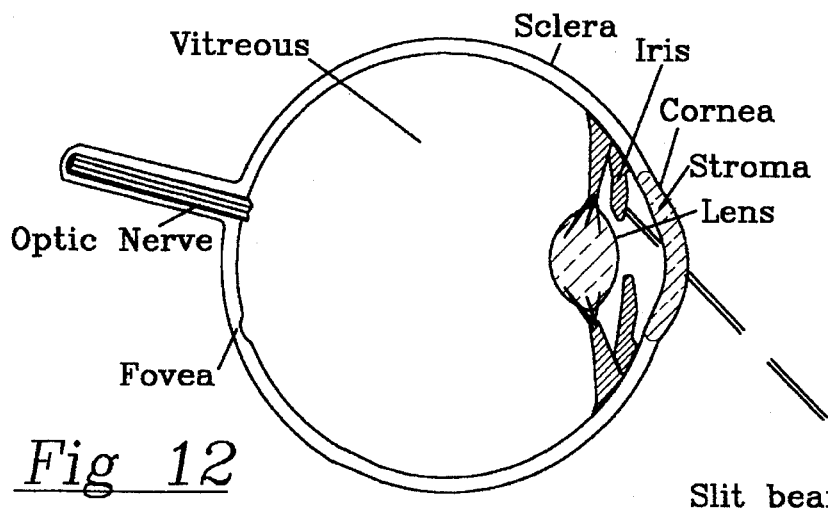
Figure 6:
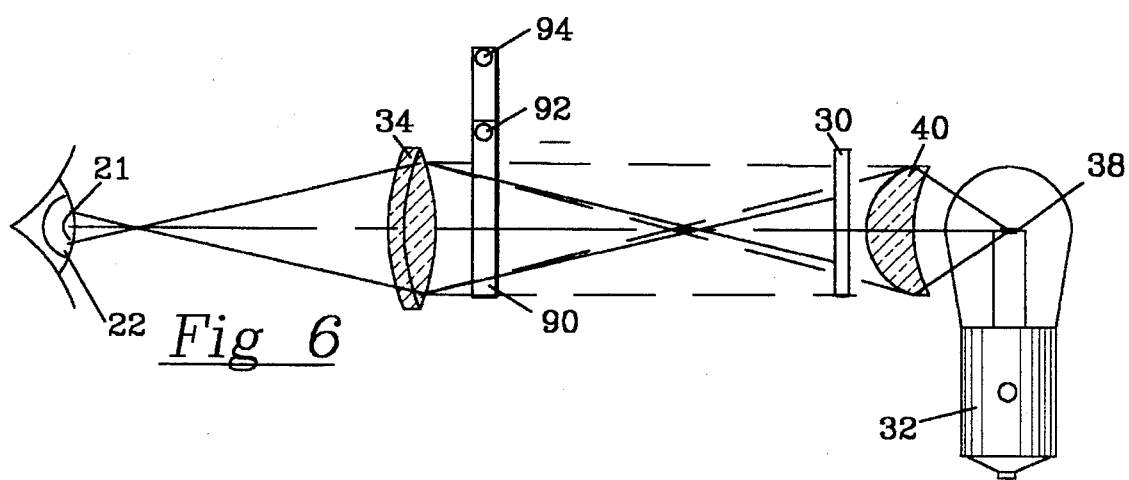
Figure 7A:
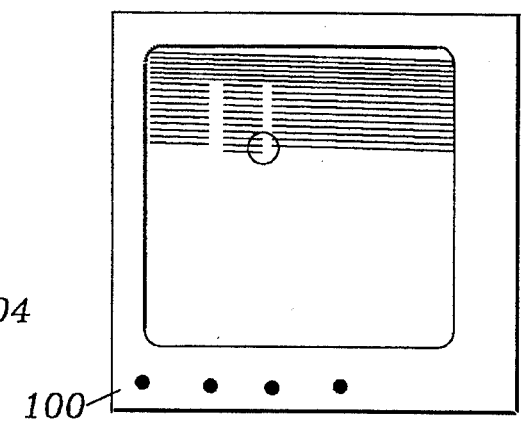
Figure 7B:
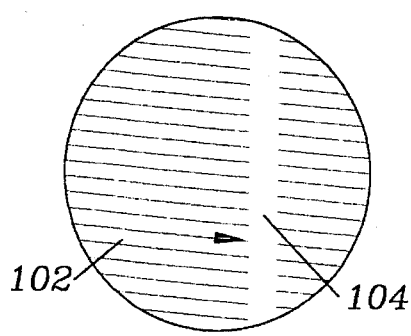
Figure 9:
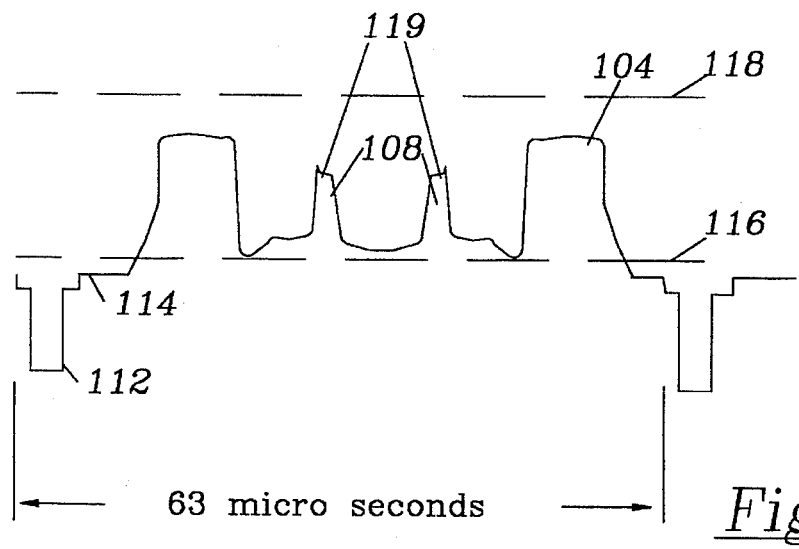
Figure 10A:
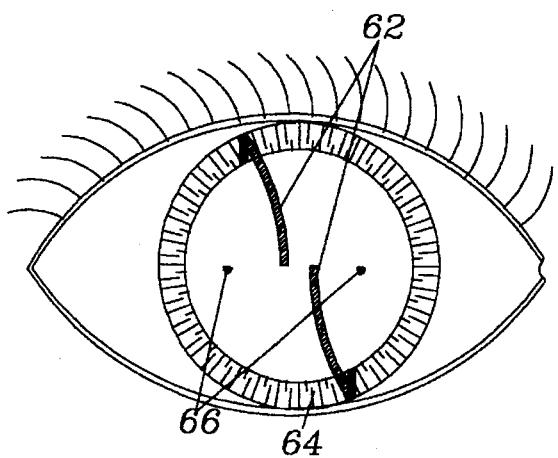
Figure 10B:
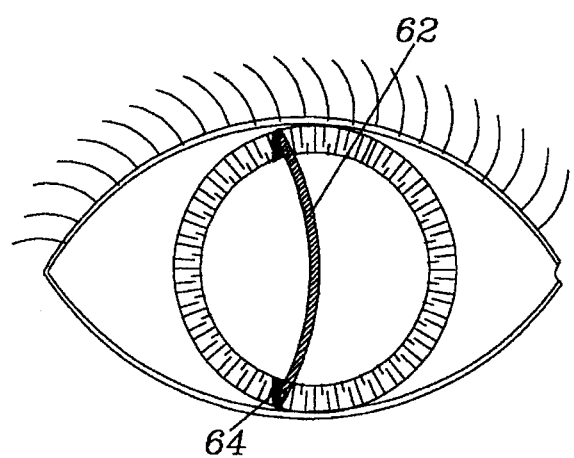
Figure 8:
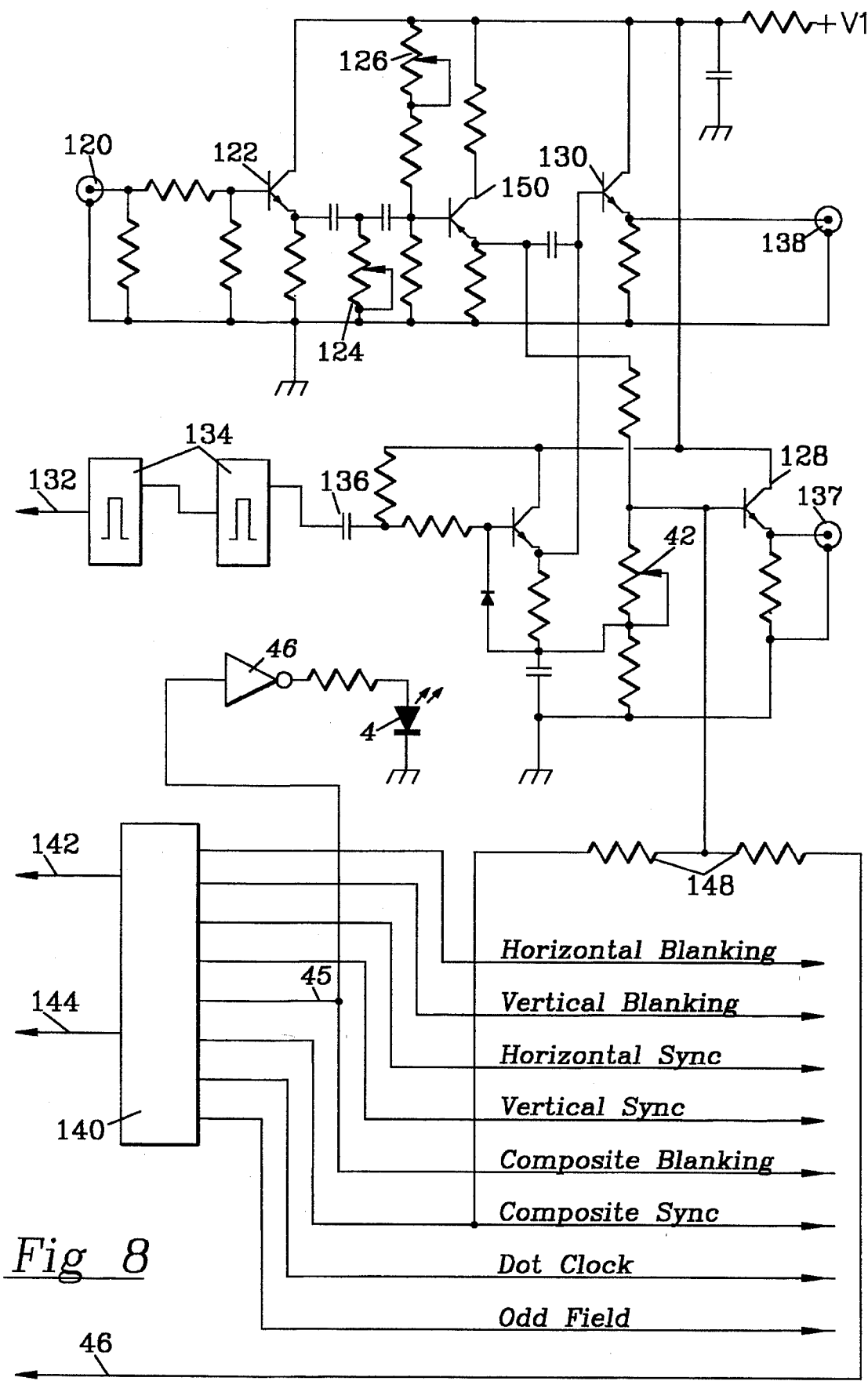
Figure 14:
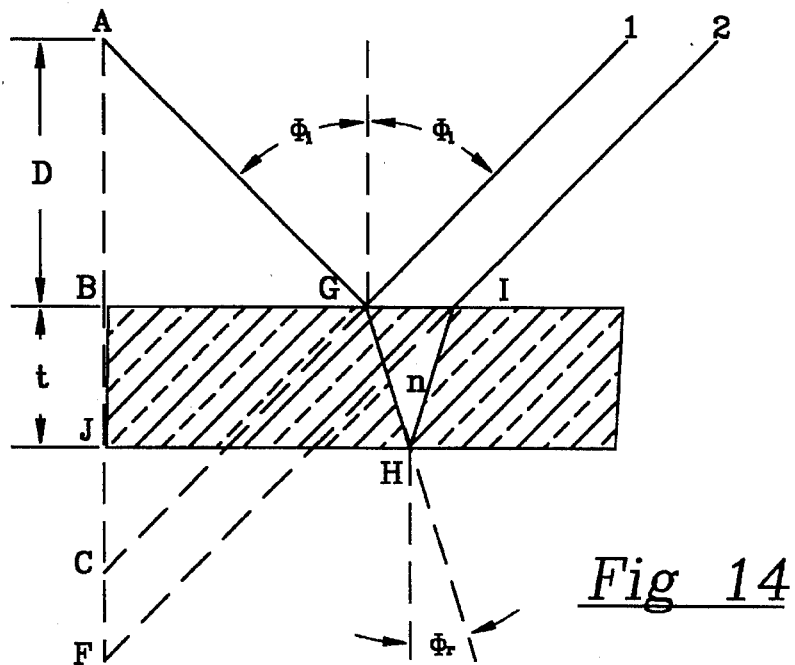
Figure 15:
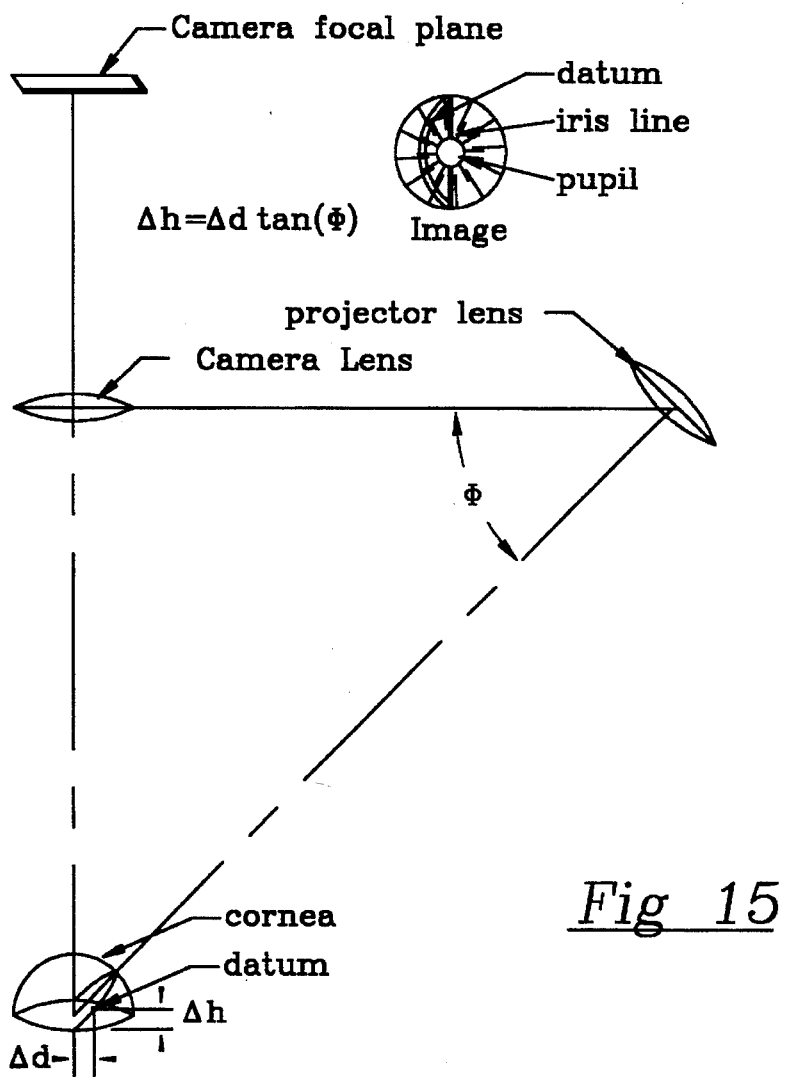

Having thus described the invention in general terms, reference will now be made to the accompanying drawings (seven sheets) in which:

FIG. 1 is a schematic view showing some of the major components of the system of the present invention;

FIG. 2 is a top plan view, partially in horizontal section, of the optical pachymeter constructed in accordance with and embodying the present invention;

FIG. 3 is a perspective view of an alternate construction of a focus aid mechanism forming part of the system of the present invention;

FIG. 4 is a front elevational view of the ophthalmic pachymeter of the present invention;

FIG. 5 is a side elevational view of the ophthalmic pachymeter of the present invention, partially in section, and illustrating the major components in the interior thereof;

FIG. 6 is a schematic view showing the optics and optical paths involved in producing a slit image at the eye of a subject;

FIG. 7A is a plan view of a television screen forming part of the television 20 used in the system of the present invention;

FIG. 7B is a plan view of a portion of a television raster shown in the circled portion of FIG. 7A;

FIG. 8 is a schematic diagram of a portion of the electric circuitry employed in the system of the present invention;

FIG. 9 is a graphical illustration showing a television wave form which may be produced in the system of the present invention;

FIG. 10A illustrates a front elevational view of the eye with half-Tyndall images for focus and alignment superimposed;

FIG. 10B illustrates a front elevational view of the eye, similar to FIG. 10A, with the half Tyndall images aligned and in the position where they would be centered in a fiducial mark;

FIG. 11 is a schematic view showing the fiducial figure employed for alignment in the present invention;

FIG. 12 is an illustration of a horizontal cross section of the eye for reference purposes;

FIG. 13 is a graphical illustration showing the geometry of the image analysis employed in the Placido method and in the present invention;

FIG. 14 is a schematic illustration of an optical ray trace for deriving thickness of a transparent member, and FIG. 15 is a schematic illustration showing the geometric relationship of the image obtained in accordance with the present invention with respect to a projector lens and camera lens.

DETAILED DESCRIPTION OF PREFERRED EMBODIMENTS

Referring now in more detail and by reference characters to the drawings, and particularly to FIG. 1, it can be seen that the ophthalmic pachymeter of the present invention comprises a television camera 20 having a conventional lens and which is aligned with and receives an image of the eye 22 of a subject through a beam splitter 24 for later quantification and for providing a television image of the eye for analysis. Referring to FIG. 3, it can be seen that the apparatus comprises a conventional incremental motor 26 for positioning an elongate aperture, e.g. a slit 28, of a slit form 30 in the focal plane of light projector represented in FIG. 1 by a lamp 32. The slit form 30 may be operatively connected to a suitable slide assembly 31, as also best illustrated in FIG. 3 of the drawings.

The slit form 30, and particularly the slit 28 thereof, in conjunction with the lamp 32, will produce an image at the eye 22 through the action of a projection lens 34 as shown in FIG. 1 for selecting sequential images for analysis. Referring now to FIG. 6, there is illustrated a Köhler arrangement 36 which comprises the lamp 32 having a dense filament 38. In this case, by further reference to FIG. 6, it can be seen that the image of the filament 38 is formed at the entrance pupil of the projection lens 34 by means of a condenser lens 40.

Adjacent to the condenser lens 40 and in optical alignment with the condenser lens 40 is the slit form 30 carrying the optical slit 28. This slit form 30 is preferably mounted on a carrier (not shown in detail). The carrier is in a direction perpendicular to the slit 28 by the aforesaid incremental motor 26. The images of the slits are brought into focus in the same plane as the television camera 20 by the projection lens 34 and a system of mirrors and prisms including a regular mirror 42 and a dichroic mirror 42', (both being interchangeable) as shown in FIGS. 1, 2, 4 and 5. A fixation lamp 44, sometimes referred to as a "target lamp" or "fixation target lamp", as shown in FIG. 1, is also provided for operation with the beam splitter 24, as shown. This combination of the lamp 32, lenses 34 and 40 and mirrors and prisms 42, as well as the slit form 30, function as a slit lamp projector.

Referring again to FIG. 1, it can be seen that the television camera 20 generates a signal representative of the image of the eye which is transmitted to a video amplifier 46 for amplification and mixing video signals for analysis. A flash analog-to-digital converter 48 receives the output of the video amplifier 46 for processing and digitizing analog signals received from the television camera 20. A data buffer 50 receives an output from the analog-to-digital converter 48 for directing the digital data to and from a storage in the for of a digital data memory 52. For example, the data buffer 50 and the data memory 52 may form part of a conventional computer which is not illustrated in detail herein. In this respect, it can be observed that many of the components are shown in schematic form (rectangular boxes) in FIG. 1.

The digital data which is directed to the digital data memory 52 constitutes a storage of the numerical brightness of each element within the fiducial boundary. An address counter 54 is provided for determining the location and storage of the pixel brightness data for each pixel in the image. A mode controller 56 is connected to the address counter 54 and is provided for determining the sequence of operations of the system. The mode controller 56 receives an input from a computer interface 58 which, in turn is connected to the data buffer 50 and is also connected to the analog-to-digital converter 48, as illustrated in FIG. 1.

The computer interface 58, operating in conjunction with a computer, controls the system elements through the associated computer. In this case, a display driver 60 is provided for controlling the aforesaid fixation target lamp 44 visible by reflection by the beam splitter 24. This serves to render the apparent location of the fixation target lamp 44, namely from the beam splitter. 24 coincident with the optical center of the television camera 20 and its associated lens system. A pulse shaper 71 receives an output from the computer interface 58 and provides a control to the display driver 60 and the camera 20.

Turning now to FIG. 10, it can be observed that there is a representative image of the eye 22. The slit beam 28 illuminated anatomical features are visible as a Tyndall image 62 representing those portions of the eye, such as the corneal epithelium, the stroma and the endothelial layer which scatter the light. An iris 64 in the eye is not the area to be measured and therefore, the illumination of this area is an artefact of Tyndall illumination. The iris image 64 may further be diminished by limiting the spectral distribution of the slit beam 28 through the use of a color filter (not shown). In addition, a slit projector, or slit projectors if more than one is used, produce specular reflections 66, as shown in FIG. 10A, and which are located in "X, Y" coordinate space, depending upon the surface curvature of the cornea of the eye 22. The associated computer, through the action of the computer interface 58 and the mode controller 56 and display driver 60 (see FIG. 1), restrict the sample data to the corneal section 62 of the eye made visible by slit illumination. The iris 64 may be dilated maximally to provide a uniform dark background for the optical section and the slit height, which is restricted to eliminate bright reflections above and below the area of interest.

The operator of the ophthalmic pachymeter is provided with a computer-generated figure which is used as a fiducial mark system illustrated by reference number 68 in FIG. 11. The fiducial marks in this fiducial mark system 68 are located around the center of the display monitor. The figure is preferably software-controlled to coincide with operation of the incremental or "stepper" motor 26 which moves the slit form 30 and hence, a half slit 160 also in this form 30. Thus, the computer generated fiducial marks are designed to be coincident with the slit position so that the operator is provided with a focus and alignment aid.

Referring now to FIGS. 4 and 5, it can be seen that the slit lamp illuminator components, e.g. the lamp 32 and slit form 30, as well as the television camera system 20 are mounted on a moveable base 70 which comprises a frame casting. A vertical positioning element, in the nature of a vertically arranged support shaft 72 is operative mounted on the base casting 70, as illustrated. Generally axles 74 which support toothed wheels (not shown) are located in the base casting 70, as best shown in FIG. 5, for motion toward and away from the subject. The device also comprises dust covers 78 which cover the toothed wheels. A friction creating member 76 is operated by a lever or handle 82 against the table surface 80 to cause the instrument to be moved by the operator for focusing and alignment. This arrangement allows for motion toward and away from the subject, as indicated. The base casting 70 is provided with internal bearings (not shown) to permit the assembly to move transversely, that is perpendicular to the forward and backward motion parallel to the optical axis of the instrument. The toothed wheels 76, located under the dust covers 78, serve to constrain the motion relative to a table 80 and hence, the patient so that movement occurs only in a specified area.

The vertical positioning element, such as the support shaft 72, raises and lowers the instrument relative to the subject to permit centering of the image in the television picture. The subject is positioned at the table 80 with a table-mounted chin and brow rest of conventional design for positioning and stabilizing the head during the measurement. Inasmuch as this chin and brow rest is of a conventional construction, it is neither illustrated nor described in any further detail herein. However, the base casting 70 is provided with the upstanding handle 82 for manual manipulation by an operator of the apparatus to enable positioning of the instrument with respect to a subject and which is also hereinafter described in more detail.

The beam splitter 24 may be mounted on the base plate 84 of a housing 86 which houses many of the components of the ophthalmic pachymeter, such as, for example, the television camera 20 the condenser lenses 40, the slit form 30, the lamp 32 and the mirrors and/or prisms 42. Located beneath the beam splitter 24 is a printed circuit assembly (not shown). This printed circuit assembly may contain the fixation lamp 44. Otherwise, the fixation lamp 44 may be mounted above the beam splitter 24 in the manner as best illustrated in FIGS. 4 and 5 of the drawings. This beam splitter 24 and the fixation target lamp 44 provide a bright target for determining the point of gaze for the subject. The brightness of this target may be controlled to permit persons with low visual acuity to perceive it and to fixate upon it.

In a more preferred embodiment of the invention, the fixation lamp 44 is preferably a light-emitting diode-type lamp and is preferably bi-colored with pulse drive to present a visible pulse stream of alternative colors at about a one second interval rate. The use of this type of fixation lamp 44 and the associated drive provides a wide range of brightness so that the target can be fixated upon by the subject irrespective of visual acuity of the subject. The co-axial location of the fixation target assures maximal ability to accurately reconstruct the three dimensional data. The fixation lamp 44, which causes the iris 64 and the sclera to be illuminated, not only provide for an image of the eye, but also enable an image to be generated for record-keeping purposes.

The normal illumination levels, when slit images are being recorded, is usually inadequate to cause surrounding tissue to be well defined for overall viewing. The common slit lamp camera uses the optical system of the bio-microscope and due to the length of the focal ratio of these systems. A large amount of flash energy is required for exposures. The present invention, however, provides a much more efficient optical design and thus, the flash energy is reduced by orders of magnitude, when compared to conventional slit lamp photography. The reduction of light energy entering into the eye is, of course, a desirable feature for subject safety and comfort, and also ensures more reliable data.

The operator of the ophthalmic pachymeter will position the half slit images 62, as shown in FIG. 10A, into coincidence so that, in effect, the two half-slit images form somewhat of an "S" shape, as shown in FIG. 10B. This will occur with reference to the fiducial figure 68 of FIG. 11, which is displayed for the operator, to thereby align and thereby focus the instrument. The half-slits, as shown, are effectively positioned by the computer in the optical center line of each projector. The operator moves the instrument, preferably by manual manipulation of the handle 82 in order to obtain this coincidence, as hereinafter described, in order to form this S-type image arrangement. When the S-type Tyndall image has been formed of the half Tyndall images, the operator may then take the necessary data.

The motors 26 which move the slit form 30 will slew the full length slits 28 of FIG. 3 across the eye from each side sequentially to provide the data sequence which will ultimately be stored for analysis. The data is masked by software in order to eliminate extraneous material. The arc of the Tyndall images lies on only one side of the iris section illuminated by the light which is passed through the cornea and has a definable maximum number of pixel loci at the apex from the iris line. The area of this pixel loci is defined by software within the system for each frame and only the data which falls within this defined area is stored for analysis. As a possible exception, a small area at the center which contains the reflection of the fixation lamp may also be stored for compensation of involuntary movements of the eye.

As indicated previously, the operator of the pachymeter can position the half-slits images 62. This can be accomplised by manual manipulation of the handle 82 in order to position the television camera 20 in three dimensional space relative to the eye. The desired alignment is obtained by viewing the display before recordation of the data to be analyzed. The generation and positioning of the box, circle or other limiting fiducial marking is by well known computer techniques that are not detailed herein. The operator simply adjusts the controls so that the optical sections coincide at the center of the display monitor. This action assures the operator that the focus and area being measured are correct. The focus and image location are simultaneously adjusted by the operator with reference to the display that shows the image from the camera with the fiducial markings superimposed.

A picture formation of a Tyndall image 62 is generated in the television camera 20. A given point on the Tyndall image 62 is projected onto the photo-sensitive area of the television camera 20. The datum of this given point on the Tyndall image, after an analog-to-digital conversion, represents an X, Y locus with associated brightness. The slit 28 positioned under computer control by the incremental motor 26 is at a known location relative to the optical centerline of the camera 20.

The projector optical axis relating to the camera axis is established in manufacture at a known angular relationship. Since that angle is known, the magnification is known and that the slit position is also known, the angle $\Phi$ is thereby defined in the associated computer software. The height of the datum above the reference plane $\Delta h$ is then calculated. Each raster line intersection with the Tyndall image 62 is used to calculate the associated height value. After the series of images which comprise a complete measurement are so defined and stored in the computer memory, the surface contour for both surfaces of the cornea and the local thickness are displayed for use.

The image which is generated may be identified as either a left eye image or a right eye image by means of a switch (not shown) and which can be located in the instrument base and which is also interfaced to the computer. With this identification, the location of the cursor in the fiducial image 68 is determined in the computer software. A transducer (not shown) may be utilized to provide a signal representative of instrument lateral displacement and is interpreted to determine the eye being examined, due to the fact that the slit lamp 32 is always displaced in the temporal direction for use.

In the preferred embodiment, a point at the vertical center of the cursor in the fiducial FIG. 68, displaced a few pixels toward one side, is identified in the software and can serve as a sample for black clamping of the video signal and which is usually accomplished by conventional circuitry. The image of the cornea is located and stored by computer software, based on known characteristics of the corneal image. All initial pixel values for the enclosed line segments of the corneal image, so identified, are averaged for reflected light intensity in terms of pixel brightness and the resultant numerical constant is used to determine the optical character of the remainder of the Tyndall image 62. After determination of the corneal pixel loci, the corneal thickness is derived by known magnification projection angle, surface shape and pixel pitch. The data are then stored by location in an area of the memory for later use.

Referring again to FIG. 6 which indicates a Köhler projector, it can be seen that the image of the slits are brought into focus in the same plane as the television camera 20 by the projection lens 34 and the system of mirrors or prisms 42, as previously described. The beam path is folded by the mirrors or prisms 42 in order to achieve compact assembly. The focal length of the projection lenses 34 is made to be as long as possible to reduce beam convergence or divergence at the eye which would otherwise degrade the Tyndall image 62.

In general, the projection lens 34 is selected to provide an aperture sine function on the order of 0.05 or less for best results. The aperture sine is calculated from the optical components by the formula; $f/d^2$ where f is the focal ratio of the lens and d is the distance from the slit to the exit pupil. The brightness of the slit image E is calculated by the formula, $E = (f/d^2)DB$, where D is the optical transmission factor for the lens and B is the luminance of the filament source, e.g. the filament 38. The use of aspheric condenser lenses, optical coatings for all surfaces and a low ratio beam splitter for the fixation target permit the use of lamps in the range of 20 Watts that provide over 400 Lumens as the light source. The minimum brightness level of the slit image reflection is dependent upon the sensitivity of the camera employed. The reflected light is on the order of 4% or less of the incident light and the greater the illumination level of the diffuse reflection, the better the signal to noise ratio of the resultant television signal.

The use of halogen cycle lamps improves the stability of light output with time and provides the best available lamp design. In addition one or more optical filters 90 located on a support pivoted to the housing 86 by a pivot pin 92 and positionable by a handle 94 (FIG. 5), or computer controlled mechanism (not illustrated), are included in the illumination path for selected illumination wave band determination. The optical filter 90 also serves to limit energy delivered to the eye 22 to reduce the possibility of photo-toxic reaction hazard to the subject. The optical filter 90 for this purpose has little or no ultra-violet or infra-red transparency.

The television display is in the form of a raster as shown in FIG. 7. The television has a monitor 100 which displays the visual information in time sequence. The beam current is low for black areas 102 and high for white areas 104 and scaled in magnitude to recreate the brightness range of the original scene. The television camera 20 generates the voltage analog of scene illumination that is provided with synchronizing signals to assure that the time sequence as reproduced is a faithful recreation of the scene being photographed.

IMAGE PROCESSING AND OPERATION

The following section more specifically describes the process employed in determining thickness and topography of the cornea. However, and while the circuitry as shown in FIG. 8, literally constitutes a part of the apparatus, it is nevertheless described in connection with this image processing and operation, since it is integrally related to the image processing and operation.

In FIG. 13, the relationship between the Tyndall image 62 and the topography of the cornea is shown. Along each raster line in the television display, there is a detectable edge of the Tyndall image which has a virtual image location displaced by delta d ($\Delta d$). This displacement distance is from the point at which the beam would have intersected the optical axis, if undeflected, as best shown in FIG. 15. From this image pixel locus the height of the datum above the reference plane, delta h ($\Delta h$), can be calculated. The calculations are performed for all intercepts in all data frames to provide a matrix of X coordinate loci from which the topography can be plotted.

Referring now to FIG. 9, the voltage waveform produced by the television camera of the pachymeter, is illustrated. As indicated previously, the beam is low for black areas 102 and high for brighter areas 104. The brightness amplitude ratio of the anterior edge of the corneal section to the dark pupillary area representing the anterior chamber is used as a reference value for lens reflection assessment. The pixel amplitudes for all elements of the reference areas are averaged to provide the baseline reflectance value.

The television signal voltage wave form, as shown in FIG. 9 is a single raster line of video information in which there are bright areas 108 from the image of the cornea and a brighter image of the iris 64 (represented by the bright areas 104) illuminated by the slit beam after the latter passes through the cornea. A sync pulse signal 112 precedes each line of pictorial information carrying voltage levels. After the sync pulse 112 a short period of a low level blanking pulses 114 follows. The blanking pulse 114 insures that the display is off while the beam is retraced to the start of a new line. The black level, represented by reference numeral 116, is the most negative of the pictorial data voltages in the video composite signal. This level is determined by a keyed clamp circuit of conventional design where a selected spot in the image representing the anterior chamber signal is sampled and used as a minimum brightness determinant. As the voltage increases, the brightness also increases in the displayed image from black to peak white 118 representing saturation of the signal. The voltage level produced at saturation by a "white" image 118 is shown by the dotted line at the top of the illustration. The brightness profile of the corneal image will vary as the local optical density and index of refraction varies.

At the leading edge in time of the corneal reflex signal, the signal rises to a peak 119 which represents the cornea to air interface. The amplitude of this signal is quite constant from subject to subject and from time to time. This constant interface signal is used for signal reference against which reflex measurements are made to quantify corneal transparency. Each succeeding raster line will then provide a density profile for a different portion of the cornea.

In the preferred embodiment of the present invention, the optical slit form 30 is moved in small lateral increments by the incremental motor 26 for sequential data sampling. In an alternative embodiment, the optical slit for form, 30 and incremental motor 26 are replaced by rhonchi rulings of suitable pattern dimension to provide several parallel slit beams in a single exposure. The plural beam system reduces the time required for data acquisition but complicates the computer processing of the data from the Tyndall images 62. In a further alternative embodiment, the slit 28 can be replaced by a liquid crystal display element so structured as to form electronically selected transparent areas substantially equivalent to the various slit positions in the preferred embodiment of this invention.

Each exposure containing the Tyndall image or images 62, is converted to digital form by the analog to digital converter 48. Through the action of the data buffer 50, the mode controller 56 the address counter 54 and the digital data memory 52 these sequential amplitude values are stored for use. The data in storage represents the pixel brightness versus locus for each slice of the cornea to be analyzed. Each successive pixel of each successive frame is then multiplied by a constant derived from the cornea to air interface signal average and the optical constant that corrects for the lower normal brightness. As each point is calculated, it is returned to storage in the same sequence for later computation and display. Tyndall illumination provides three-dimensional data sequences of data that are transferred to the computer by the action of the computer interface 58. In an area scan using the apparatus of the present invention, the processing time is so small compared to the user's ability to resolve time that the actual imaging takes place on a real time basis. In other words, the analysis and determinations, e.g., optical thickness, are made on a real time basis.

FIG. 8 represents a schematic diagram of part of the electronic circuitry employed in the preferred embodiment of the present invention. The composite video signal from the television camera 20 is applied to the input 120 of a signal conditioning amplifier. The terminated signal is buffered by an emitter follower 122 which drives DC restoration and sync stripper networks 124 and 126. The DC restored and limited video is buffered by a second emitter follower and serves to drive clamping and mixing amplifiers 128 and 130.

A computer derived black reference timing signal 132 is generated in temporal synchronism with the area of the picture from the television camera 20 which defines the pupillary area near the center of the picture. This pulse is conditioned by mono-stable circuits 134 to provide a constant amplitude and constant width sampling pulse. This sampling pulse, via a capacitor 136 allows the capacitor to store a voltage sample of the raw video that represents the "black" level. The black reference level thus generated biases the amplifier 130 for use in the analog to digital converter 48. The signals representative of reference levels are received at output nodes 137 and 138, as shown in FIG. 8.

Signals from the computer are used for regeneration of the television timing in a conventional integrated circuit device 140 which makes use of a composite sync signal 142 and dot clock signal 144 from the computer display driver. The computer generated fiducial signal 146 and regenerated composite sync are mixed via resistors 148 with the video signal from an emitter follower 150 for providing the monitor signal. The monitor signal is used to drive a conventional CRT display for use as a viewfinder by the user of the pachymeter of the present invention. A potentiometer 242 is provided for setting sync injection amplitude to conform to IRE or SMPTE standards.

The display of the data can take the form of a single frame's information that can be displayed as false colored areas for relative transparency, for example. The entire set of frames may be combined to form a virtual three-dimensional display of surface contour or membrane thickness as needed. The data also may be presented simply as a numerical value for average optical density, density area or other forms that the user finds most useful, by the use of well-known display techniques. In most, if not all cases, the exact optical density profile is of less interest to the clinician than the shape and thickness. For example, in refractive surgery, the incision depth should be at least ninety percent of the local corneal thickness without total penetration.

When a suitable image or sequence of images has been stored and the requisite computations performed in the computer, the digital information that defines the cornea can be displayed in some arbitrary color upon the monitor together with the alphanumeric information image from computer by conventional video mixer means. Alternatively the data may be presented for use in any of several formats such as plotted graphs, tabular numerical form, pseudo three dimensional shaded surface plots or other formats that are well known in the art.

Referring again FIG. 3, the motion imparted to the slit form or so-called slit carrier member is controlled by the computer through the action of the incremental stepper motor 26. In an alternative embodiment a second slit 160 of lesser length than the slit 28 is provided in both beam projection paths for the purpose of focusing the instrument. The two half slits so produced are placed by the operator into contact at the point of reflection of the fixation lamp 44 to establish proper alignment prior to recordation of the image sequence.

Thus, there has been illustrated and described a unique and novel ophthalmic pachymeter which enables determination of the thickness and relative optical density of the cornea on a real-time basis and which thereby fulfills all of the objects and advantages which have been sought. It should be understood that many changes, modifications, variations and other uses and applications will become apparent to those skilled in the art after considering this specification and the accompanying drawings. Therefore, any and all such changes, modifications, variations and other uses and applications which do not depart from the spirit and scope of the invention, are deemed to be covered by the invention.

Having thus described the invention, what I desire to claim and secure by letters patent is:

1. An ophthalmic pachymeter for aiding in determining one or more physical characteristics of the anterior segment of the eye, comprising:
   a) light projector means including a slit means for illuminating defined areas of the cornea;
   b) imaging means for providing a television image of selected portions of the illuminated areas of the eye as illuminated by the projector means;
   c) means for causing a movement of the slit means relative to the anterior segment of the eye to obtain a series of selected images of the eye;
   d) video means cooperatively located with respect to the projector means for receiving the images of the selected portions of the eye and for generating and transmitting a video signal representative of the images of the eye;
   e) converter means for converting portions of the video signal into digital format; and
   f) an analysis means for detecting and storing relative brightness levels within the defined areas and which brightness levels are directly correlated to the one or more physical characteristics to be determined.

2. An ophthalmic pachymeter according to claim 1, further comprising a means for defining data points based upon relative numerical values detected by the converter means.

3. An ophthalmic pachymeter according to claim 2, further comprising means responsive to the data points for defining a reference level.

4. An ophthalmic pachymeter according to claim 1 further comprising means for locating the light projector means relative to the cornea so that an instantaneous position of the slit means constitutes a masking means for delineating a portion of the video signal to be converted into digital format to define the shape of the cornea.

5. The ophthalmic pachymeter according to claim 1 wherein said pachymeter is located with respect to an eye for aiding in determining physical characteristics comprising thickness and surface contour of the anterior segment of the eye, and the analysis means receiving the video signal in digital format and operating in conjunction with a processing means for determining the thickness of the eye anterior segment and the surface contour thereof.

6. A densitometer for aiding in determining the thickness and relative optical density of the cornea of an eye on a real-time basis, said densitometer comprising:
   a) slit projector means for illuminating portions of the cornea of the eye;
   b) imaging means for generating a series of television images of sequential individual segments of the portions of the cornea of the eye illuminated by the slit projector means;
   c) converter means for converting the television images into digitally encoded images;
   d) illumination means for illuminating individual preselected areas of the cornea of the eye in which the digitally encoded images are to be generated and which operates in conjunction with the slit projector means;
   e) processing means for receiving the digitally encoded images from the slit projector means and generating data used in the determination of the thickness and of the optical density of the cornea said processing means generating the data related to the digitally encoded images at substantially the same time that the digitally encoded television images of the eye are being generated;

f) storage means associated with the processing means for receiving and storing the processed digitally encoded television images in digital format; and g) means operatively connected to the storage means for regenerating the images which were stored in the storage means.

7. The densitometer according to claim 6 wherein the digitally encoded images are comprised of a plurality of digital data points and the densitometer further comprises discriminator means for reducing the number of digital data points in the digitally encoded images processed by the processing means.

8. The densitometer according to claim 7 wherein the discriminator means operates in conjunction with the processing means to reduce the number of data points processed to define each significant element on a reflected image of an anterior portion of the eye.

9. The densitometer according to claim 6 wherein a corneal-air interface is compared with a corrected reflectance of the stroma and the endothelium of the eye in order to determine relative transparency.

10. The densitometer according to claim 6 wherein an analog to digital converter means is provided for converting the television images into digital format.

11. A system for producing surface contour maps of the cornea of the eye comprising:

a) a projection illumination means for illuminating areas of the cornea for producing a definable spatial delineation of corneal contour;

b) slit image means moveable across and relative to the surface of the cornea in which a contour image is to be generated;

c) video signal generating means for rendering the illuminated areas into electrical analog signals;

d) digitizer means for conversion of the said analog signals into computer acceptable digital signals; and e) computer means for processing the digital signals and generating data to provide a determination of the corneal surface shape from said digital signals and generating control signals for generating a map of the surface contour of the cornea of the eye.

12. The system according to claim 11 wherein said system comprises program control means for controlling the computer means and to enable the computer generated control signals to be generated into a visibly displayed surface contour.

13. The system according to claim 11 wherein said video signal generating means comprises a television camera means.

14. The system according to claim 13 wherein the projection illumination means comprises a slit image projection system.

15. A densitometer for aiding in determining the thickness and relative optical density of the cornea of an eye on an real-time basis, said densitometer comprising:

a) optical projector means for illuminating a portion of the cornea of the eye;

b) an optical slit associated with the projector means for creating slit illuminated portions of the eye;

c) signal generating means for generating a series of optical images of a section of the cornea of an eye;

d) converting means for converting the video images into equivalent digital signals representative of the video images to create digitally encoded images;

e) fiducial means operating in conjunction with the converting means for delineating portions of the video images which are to be converted into digital signals;

f) processing means for receiving the digitally encoded images and providing data for determination of the thickness and relative optical density of the cornea, said signal generating means generating video images at essentially the same time as the processing means enables such determination so that the densitometer makes such determination on a real time basis; and g) storage means for receiving the digitally encoded images and storing same for later regeneration of such stored images.

16. The densitometer of claim 15 wherein the densitometer further comprises storage means associated with the processing means for receiving and storing the digital signals representative of the digitally encoded images.

17. The densitometer of claim 16 wherein the densitometer further comprises means operatively connected to the processing means for recreating the digitally encoded images stored in the memory means or recreating information about the digitally encoded images stored in the memory means.

18. The densitometer according to claim 15 wherein the digitally encoded images are composed of a plurality of digital data points, and the densitometer further comprises discriminator means for reducing the number of data points processed by the processing means.

19. In an ophthalmic pachymeter of the type which has a light source for illuminating a portion of the cornea and imaging means to enable generating television images of the cornea in conjunction with a slit moving with respect to the plane of the cornea and generating such images during the movement, an improved circuit arrangement comprising:

a) analog to digital converter means for converting analog video signals to corresponding digital signals;

b) computer interfacing means for connection to a digital computer;

c) a data memory operatively connected to said interfacing means and said analog to digital converter means for storing the corresponding digital signals;

d) a mode controller operatively connected to said computer interfacing means for determining and controlling sequence of operations;

e) driving means operatively connected to said computer interfacing means for driving a fixation light means for maintaining a fixation of the eye of a subject in relation to a slit moving with respect to the plane of the cornea.

20. An improved circuit arrangement of claim 19 comprising a data buffer means is operatively connected to said data memory and mode controller and computer interface for controlling movement of digital data.

21. An ophthalmic instrument for determining physical characteristics of an eye to aid in identifying exact and precise locations of optical discontinuities and/or aberrations of the eye, said instrument comprising:

a) a light projector means for illuminating a portion of an eye;

b) electronic imaging means for obtaining an analog signal image of illuminated portions of the eye;

c) slit means optically interposed between the light projector means and the electronic imaging means;

d) means causing relative movement of the slit means relative to the eye to enable a plurality of slit image exposures of the eye during such relative movement and generation of video image signals of such slit image exposures;

e) converter means for converting the video image signals into digital signals for digital processing; and f) processing means receiving the digital signals from the converter means for processing the signals to identify discontinuities and optical aberrations of the eye.

22. The ophthalmic instrument according to claim 21 wherein said instrument comprises a fixation target lamp for enabling fixation of an eye during imaging thereof.

23. The ophthalmic instrument of claim 21 wherein the means causing relative movement causes movement of the slit means relative to the eye and in relation to the operation of the electronic imaging means.

24. The ophthalmic instrument of claim 23 wherein the instrument measures elemental brightness of a portion of a Tyndall image of the eye.

25. The ophthalmic instrument of claim 23 wherein the instrument comprises fiducial means for delineating a portion of the eye to be imaged.

26. The ophthalmic instrument of claim 21 wherein the instrument is a pachymeter.

27. A method for ascertaining the extent of an optical aberration or an optical discontinuity of tissue of the eye comprising the steps of:

a) selectively illuminating the tissue area to be analyzed;

b) receiving and quantifying an image of the said tissue;

c) delineating the portions of the image which contains the optical aberration or optical discontinuity and also delineating a reference area;

d) converting said delineated area into digital data; and e) analyzing the relative numerical magnitude of said digital data to ascertain the severity of the optical aberration or optical discontinuity.

28. The method as recited in claim 27 further comprising the steps of establishing threshold values for said digital data, enumerating the data according to relative magnitude and location and converting the enumerated data into an area form.

29. The method as recited in claim 28 further comprising the steps of measuring a locus of data points defined in the image in terms of brightness relative to a second area and multiplying the defined locus of data points by a constant for compensation of optical losses.

30. A method for ascertaining a physical characteristic of an eye comprising the steps of:

a) selectively illuminating tissue area of the eye to be analyzed;

b) generating a series of successive images of successive portions of the illuminated tissue area;

c) receiving and quantifying the images of the said tissue area;

d) delineating portions of the images and a reference area;

e) conversion of the said portions of the images in the delineated areas into digital data; and f) analyzing the relative numerical magnitude of the said digital data to ascertain the physical characteristics of the eye.

31. The method as recited in claim 30 further comprising the steps of establishing threshold values for said digital data, enumerating said data according to relative magnitude and location and converting the enumerated data into an area form.

32. The method as recited in claim 31 further including the steps of defining the locus of points in certain of the images in terms of spatial relationship, construction of a matrix of the said locus of points to form parallel slices in space, and display of the resultant matrix as a three dimensional surface or a thickness map.

33. A method for aiding and determining the thickness and relative optical density of the cornea of an eye on a real-time basis, said method comprising:

a) illuminating a preselected area of the cornea of the eye to enable generation of digitally encoded images;

b) generating a series of digitally encoded television images of a section of the cornea of an eye;

c) processing edge data contained in the digitally encoded images to enable a display of corneal contour and thickness from said digitally encoded video images;

d) generating a display of the corneal thickness and corneal surface contour;

e) receiving and storing the processed digitally encoded images in a storage means;

f) recreating the images which were stored in the storage means; and g) using the digitally encoded images to enable the determination of thickness and relative optical density of the cornea of the eye at essentially the same time as the digitally encoded images are generated.

34. The method according to claim 33 wherein the method further comprises the step of reducing the number of digital data points in the digitally encoded images which are processed.

35. The method according to claim 34 wherein the method comprises reducing the number of data points processed to define each significant element in a reflected image of an anterior portion of the eye.

36. A method according to claim 33 wherein the method comprises comparing a corneal-air interface with a corrected reflectance of the stroma and the endothelium of the eye in order to determine relative transparency.

37. A method for aiding in determining the thickness and relative optical density of the cornea of an eye on a real-time basis, said method comprising:

a) illuminating a preselected area of the cornea of the eye in which images are to be generated;

b) generating a series of video images of a section of the cornea of an eye;

c) converting the video images into equivalent digital signals representative of the images to create digitally encoded images;

d) delineating portions of the video images which are to be converted into digital signals;

e) receiving the digitally encoded images and storing such images in a digital format; and f) using the digitally encoded images to enable a determination of the thickness and relative optical density of the cornea of the eye and at essentially the same time as the digitally encoded images are generated.

38. The method of claim 37 wherein the method further comprises recreating the images stored in memory means or information about the images stored in the memory means.

39. A method for determining physical characteristics of an eye to aid in identifying exact and precise location of optical discontinuities and/or aberrations of the eye, said method comprising:

a) illuminating a portion of an eye with a light projector means;

b) obtaining an analog signal image of illuminated portions of the eye with an electronic imaging means;

c) optically interposing a slit between the light projector means and the electronic imaging means;

d) causing relative movement of the slit relative to the eye and across the eye;

e) causing a plurality of slit image exposures of the eye during such relative movement;

f) generating video image signals of such slit image exposures;

g) converting the video image signals into digital signals for digital processing thereof to identify discontinuities and optical aberrations; and h) processing the digital signals representative of the video image signals to determine the precise location of optical discontinuities and/or aberrations of the eye and at essentially the same time as the video image signals are generated.

40. The method according to claim 39 wherein said method comprises causing fixation of an eye during imaging thereof.

41. The method according to claim 39 wherein the method comprises measuring elemental brightness of a portion of a Tyndall image of the eye.

42. The method according to claim 39 wherein the method comprises delineating a portion of the eye to be imaged.

43. A densitometer for aiding in determining the thickness and relative optical density of the cornea of an eye on an real-time basis, said densitometer comprising:

a) optical projector means for illuminating a portion of the cornea of the eye;

b) an optical slit means associated with the projector means for creating slit illuminated portions of the eye;

c) means for causing movement of the optical slit means relative to and across the cornea to obtain images of individual sections of the cornea;

d) optical slit signal generating means for generating a series of optical images of sections of the cornea of an eye;

e) converting means for converting the video images into equivalent digital signals representative of the video images to create digitally encoded images;

f) fiducial means operating in conjunction with the converting means for delineating portions of the video images which are to be converted into digital signals;

g) processing means for receiving the digitally encoded images and providing date for determination of the thickness and relative optical density of the cornea, said signal generating means generating video images at essentially the same time as the processing means enables such determination so that the densitometer makes such determination on a real time basis; and h) storage means for receiving the digitally encoded images and storing same for later regeneration of such stored images.

44. The densitometer of claim 43 wherein the densitometer further comprises storage means associated with the processing means for receiving and storing the digital signals representative of the digitally encoded images.

45. The densitometer of claim 44 wherein the densitometer further comprises means operatively connected to the processing means for recreating the digitally encoded images stored in the memory means or recreating information about the digitally encoded images stored in the memory means.

46. The densitometer according to claim 45 wherein the digitally encoded images are composed of a plurality of digital data points, and the densitometer further comprises discriminator means for reducing the number of data points processed by the processing means.

47. A method for aiding in determining the thickness and relative optical density of the cornea of any eye on a real-time basis, said method comprising:

a) illuminating a preselected area of the cornea of the eye in which images are to be generated;

b) generating a series of individual successive series of video images of individual successive sections of the cornea of an eye;

c) converting the video images into equivalent digital signals representative of the images to create digitally encoded images;

d) delineating portions of the video images which are to be converted into digital signals;

e) receiving the digitally encoded images and storing such images in a digital format; and f) using the digitally encoded images to enable a determination of the thickness and relative optical density of the cornea of the eye and at essentially the same time as the digitally encoded images are generated.

48. The method of claim 47 wherein the method further comprises recreating the images stored in memory means or information about the images stored in the memory means.

* * * * *